United States Patent
Shi et al.

(10) Patent No.: US 12,004,813 B2
(45) Date of Patent: Jun. 11, 2024

(54) LARGE FIELD-OF-VIEW ADAPTIVE OPTICS RETINAL IMAGING SYSTEM AND METHOD WITH COMMON OPTICAL PATH BEAM SCANNING

(71) Applicant: SUZHOU INSTITUTE OF BIOMEDICAL ENGINEERING AND TECHNOLOGY, CHINESE ACADEMY OF SCIENCES, Jiangsu (CN)

(72) Inventors: Guohua Shi, Jiangsu (CN); Yi He, Jiangsu (CN); Feng Gao, Jiangsu (CN); Wen Kong, Jiangsu (CN); Lina Xing, Jiangsu (CN); Wanyue Li, Jiangsu (CN); Xin Zhang, Jiangsu (CN); Jing Wang, Jiangsu (CN)

(73) Assignee: Suzhou Institute of Biomedical Engineering and Technology, Chinese Academy of Sciences, Jiangsu Province (CN)

( * ) Notice: Subject to any disclaimer, the term of this patent is extended or adjusted under 35 U.S.C. 154(b) by 841 days.

(21) Appl. No.: 16/977,192

(22) PCT Filed: Oct. 23, 2019

(86) PCT No.: PCT/CN2019/112687
§ 371 (c)(1),
(2) Date: Nov. 23, 2020

(87) PCT Pub. No.: WO2021/046975
PCT Pub. Date: Mar. 18, 2021

(65) Prior Publication Data
US 2021/0121063 A1  Apr. 29, 2021

(30) Foreign Application Priority Data
Sep. 9, 2019  (CN) .......................... 201910864687.6

(51) Int. Cl.
*A61B 3/15*  (2006.01)
*A61B 3/00*  (2006.01)
*H04N 23/58*  (2023.01)

(52) U.S. Cl.
CPC ............ *A61B 3/152* (2013.01); *A61B 3/0008* (2013.01); *H04N 23/58* (2023.01)

(58) Field of Classification Search
CPC ..... A61B 3/152; A61B 3/0008; A61B 3/1015; A61B 3/1025; A61B 3/113; A61B 3/1225;
(Continued)

(56) References Cited

U.S. PATENT DOCUMENTS

| | | | |
|---|---|---|---|
| 2007/0252951 | A1 | 11/2007 | Hammer et al. |
| 2011/0234978 | A1 | 9/2011 | Hammer et al. |

(Continued)

FOREIGN PATENT DOCUMENTS

| | | | |
|---|---|---|---|
| CN | 101862178 A | 10/2010 | |
| CN | 101884524 A | 11/2010 | |

(Continued)

OTHER PUBLICATIONS

Written Opinion of International Application No. PCT/CN2019/112687.
(Continued)

*Primary Examiner* — Balram T Parbadia
*Assistant Examiner* — Rahman Abdur
(74) *Attorney, Agent, or Firm* — Elmore Patent Law Group, P.C.; Joseph C. Zucchero; Carolyn S. Elmore

(57) ABSTRACT

A large field-of-view adaptive optics retinal imaging system and method with common optical path beam scanning, the system comprises: a light source module (1), an adaptive optics module (2), a beam scanning module (3), a defocus compensation module (4), a sight beacon module (6), a pupil monitoring module (7), a detection module (8), a control module (9) and an output module (10). The beam scanning module is configured in different scanning modes for carrying out different scanning imaging functions including a large field-of-view imaging function, a small field-of-view high-resolution imaging function and a large field-of-view high-resolution imaging function. The system is simple in structure, and the common optical path structure can obtain three types of retinal imaging images, which meets the requirements of different application scenarios and improves the application range of retinal imaging.

9 Claims, 2 Drawing Sheets

(58) Field of Classification Search
CPC ........... A61B 3/12; A61B 3/14; A61B 3/0025;
A61B 3/1241; H04N 23/58
USPC ........................................................ 351/206
See application file for complete search history.

(56) References Cited

U.S. PATENT DOCUMENTS

| | | |
|---|---|---|
| 2012/0133888 A1 | 5/2012 | Gray et al. |
| 2013/0242363 A1* | 9/2013 | Weiss .................... G02B 26/105 |
| | | 359/200.7 |
| 2015/0282707 A1 | 10/2015 | Tanabe et al. |
| 2016/0317030 A1 | 11/2016 | He et al. |
| 2017/0311796 A1 | 11/2017 | Walsh et al. |
| 2018/0092528 A1 | 4/2018 | Takeno et al. |

FOREIGN PATENT DOCUMENTS

| | | |
|---|---|---|
| CN | 102802504 A | 11/2012 |
| CN | 103393400 A | 11/2013 |
| JP | 2019048088 A | 3/2019 |

OTHER PUBLICATIONS

Webb, R.H., "Confocal Scanning Laser Ophthalmoscope," Applied Optics, vol. 26, No. 8, pp. 1492-1499 (Apr. 1987).
Office Action in EP19917523.3 dated Aug. 2, 2021.
Supplementary European Search Report in EP19917523.3 dated Jun. 18, 2021.

\* cited by examiner

LARGE FIELD-OF-VIEW ADAPTIVE OPTICS RETINAL IMAGING SYSTEM AND METHOD WITH COMMON OPTICAL PATH BEAM SCANNING

CROSS-REFERENCE TO RELATED APPLICATIONS

This application is a US National Stage entry of International Application No. PCT/CN2019/112687, filed Oct. 23, 2019, published in Chinese. This application also claims priority to Chinese Patent Application No. 201910864687.6 filed with CNIPA on Sep. 9, 2019, entitled "LARGE FIELD-OF-VIEW ADAPTIVE OPTICS RETINAL IMAGING SYSTEM AND METHOD WITH COMMON OPTICAL PATH BEAM SCANNING", the entirety of which is incorporated herein by reference.

TECHNICAL FIELD

The present application relates to the technical field of optical imaging, and in particular relates to a large field-of-view adaptive optics retinal imaging system and method with common optical path beam scanning.

BACKGROUND

In 1987, the traditional confocal scanning technology was developed into a mature laser confocal scanning imaging equipment (Webb R, Hughes G, Delori F. Confocal scanning laser ophthalmoscope. Applied optics. 1987; 26(8): 1492-9), and it is widely used in retinal imaging, which can realize large field-of-view in-vivo imaging of fundus retina. However, the eyeball is a complex optical system, and optical aberration is inevitable even in an eye without refractive error, especially in order to obtain high-resolution images at a large value of optical aperture. Higher resolution at the diffraction limit can be obtained with a larger pupil according to optical theory, but a larger pupil brings more aberration of the human eye which greatly limits the actual resolution. Traditional laser confocal scanning ophthalmoscopes can usually obtain a large field-of-view image of the eye fundus of more than 10 degrees, but it is difficult to distinguish blood vessels of less than 20 microns, let alone observe fine structures such as visual cells.

In the 1890s, with the introduction of adaptive optics technology into fundus retinal imaging, the adaptive optics deformable mirrors and other correction devices could be used to correct human eye aberrations well, so as to obtain high-resolution at the diffraction limit and realize in-vivo observation of retinal micro-vessels and visual cells for the first time. The patent application with patent number ZL201010197028.0 proposes a retinal imaging device based on adaptive optics technology. This device realizes two-dimensional synchronous scanning of the retinal plane by using two independent scanning mirrors to achieve confocal scanning imaging, which can achieve high-resolution imaging function. However, this device can only achieve high-resolution imaging of the human eye with a maximum field-of-view of 3 degrees. As limited by the halo zone in adaptive optics aberration correction, adaptive optics often makes a compromise in the field of view of imaging while realizing high-resolution imaging, and can only realize imaging in a small field of view within 3 degrees.

In summary, it can be seen that the existing laser confocal scanning ophthalmoscopes having a large field of view of imaging do not have sufficient resolution to observe fine structures of the retina; and the existing laser confocal scanning ophthalmoscopes combined with adaptive optics can observe fine structures of the retina, but have a small field of view of imaging, which makes it impossible to observe lesions in a larger field of view.

SUMMARY

The technical problem to be solved by the present application is to provide a large field-of-view adaptive optics retinal imaging system with common optical path beam scanning to overcome the above-mentioned deficiencies in the prior art.

As is well known, the existing laser confocal scanning ophthalmoscopes having a large field of view of imaging do not have sufficient resolution to observe fine structures of the retina; and the existing laser confocal scanning ophthalmoscopes combined with adaptive optics can observe fine structures of the retina, but have a small field of view of imaging, which makes it impossible to observe lesions in a larger field of view.

As compared with the technical achievements in the field of laser confocal scanning imaging at home and abroad, the present application proposes a large field-of-view adaptive optics retinal imaging system with common optical path beam scanning based on the basic principles of a combination of adaptive optics and confocal scanning technology, wherein two scanning mirrors are used to form a common optical path structure, the two scanning mirrors are configured in different scanning modes, which can perform large field-of-view imaging of more than 20 degrees on the retina for observing lesion distribution areas of retinal disease, and can also perform small field-of-view imaging of no more than 5 degrees on the retina, and with correction of aberration by adaptive optics, small field-of-view high-resolution imaging can be realized to observe fine structures and pathological changes of the lesion, and a second scanning mirror is further configured to perform sequential tilted illumination of the light beam in each area of the retina, and then, by image stitching, a large field-of-view high-resolution imaging of the retina over 15 degrees can be acquired at one time.

The technical solution adopted in the present application is a large field-of-view adaptive optics retinal imaging system with common optical path beam scanning which comprises: a light source module, an adaptive optics module, a beam scanning module, a defocus compensation module, a sight beacon module, a pupil monitoring module, a detection module, a control module and an output module;

the light source module is configured to emit a parallel light beam, wherein the parallel light beam irradiates a human eye after sequentially going through the adaptive optics module, the beam scanning module and the defocus compensation module, imaging light that is scattered by the human eye and carries aberration information of the human eye and light intensity information returns along an original optical path of the parallel light beam and reaches the adaptive optics module and the detection module;

the adaptive optics module is configured to receive the imaging light carrying the aberration information of the human eye, and perform real-time measurement and correction of aberration of the human eye;

the beam scanning module is controlled by the control module, and the beam scanning module is configured in different scanning modes for carrying out different scanning imaging functions at least including a large field-of-view imaging function, a small field-of-view high-resolution imaging function and a large field-of-view high-resolution imaging function;

the defocus compensation module is configured to achieve compensation of refractive error of the human eye;

the sight beacon module is configured to guide and fix a sight beacon in different areas of a retina of the human eye;

the pupil monitoring module is configured to align and monitor a pupil of the human eye;

the detection module is configured to acquire the returning imaging light of the human eye, convert the imaging light into an electrical signal, and transmit the electrical signal to the control module; and the output module is configured to connect to the control module, and display and store imaging images of the human eye.

Preferably, the light source module, the adaptive optics module, the beam scanning module, the sight beacon module, the defocus compensation module and the pupil monitoring module are sequentially arranged along an incident optical path;

the light source module is configured to comprise a light source, a collimator and a first beam splitter that are sequentially arranged along the incident optical path, and is configured to output a parallel light beam to the adaptive optics module, wherein the light emitted by the light source passes through the collimator, and is then partially transmitted through the first beam splitter to enter the adaptive optics module;

the adaptive optics module is configured to comprise a second beam splitter, a wavefront corrector, a transmissive or reflective telescope and a wavefront sensor that are sequentially arranged along the incident optical path, and is configured to connect to the beam scanning module, detect and correct wavefront aberration; the parallel light beam output by the light source module, after partially being transmitted through the second beam splitter, is reflected to the transmissive or reflective telescope by the wavefront corrector to enter the beam scanning module; the returning imaging light carrying the aberration information of the human eye and the light intensity information exits from the beam scanning module and enters the transmissive or reflective telescope, and then is reflected to the second beam splitter by the wavefront corrector; part of the imaging light is reflected to the wavefront sensor by the second beam splitter to realize measurement of wavefront aberration, and the rest of the imaging light is transmitted through the second beam splitter to continue to propagate;

the wavefront sensor is configured to receive an imaging light beam containing the aberration information of the human eye and transmit the aberration information to the control module, and the control module is configured to perform wavefront calculation, obtain a wavefront control voltage and output the wavefront control voltage to the wavefront corrector, so as to detect and correct wavefront aberration.

Preferably, the detection module is configured to comprise a collection lens, a confocal pinhole and a high sensitivity detector, wherein the part of the returning imaging light that is transmitted through the second beam splitter of the adaptive optics module reaches the first beam splitter, and is partially reflected by the first beam splitter to the collection lens, focused by the collection lens and then passes through the confocal pinhole to reach the high sensitivity detector, a photoelectric conversion is performed by the high sensitivity detector to obtain an electrical signal, then the electrical signal is output to the control module for processing to obtain a retinal imaging image, and finally the retinal imaging image is output to the output module for display and storage;

the confocal pinhole is disposed at a focal point of the collection lens.

Preferably, the beam scanning module is configured to comprise a first scanning mirror and a second scanning mirror, and the two scanning mirrors are connected through a transmissive or reflective telescope to achieve pupil plane matching; the first scanning mirror is configured to perform transverse scanning of the retinal plane, the second scanning mirror is configured to perform vertical scanning of the retinal plane under the driving of a periodic voltage, the second scanning mirror is able to generate a certain transverse and vertical inclination angle under the driving of a DC voltage, the second scanning mirror is also able to perform transverse and vertical two-dimensional scanning of the retinal plane under the driving of a periodic voltage at the same time of generating the transverse and vertical inclination angle under the driving of a DC voltage;

the first scanning mirror and the second scanning mirror can have their front and rear positions interchanged;

the beam scanning module is controlled by a voltage signal output from the control module and is configurable in different scanning modes for carrying out different imaging functions including a large field-of-view imaging function, a small field-of-view high-resolution imaging function and a large field-of-view high-resolution imaging function.

Preferably, the defocus compensation module is configured to comprise a scanning objective lens, a flat-field objective lens and a guide rail that are sequentially arranged along the incident optical path, the light beam exiting from the beam scanning module propagates to the pupil monitoring module through the defocus compensation module, and the flat-field objective lens can reciprocate along the central axis of the flat-field objective lens on the guide rail to achieve the compensation of refractive error of the human eye.

Preferably, the sight beacon module is configured to comprise an LED array, a lens and a first dichroic beam splitter, wherein the light emitted by any one of LED beads in the LED array after being lit by the control module propagates through the lens, is reflected by the first dichroic mirror to enter the defocus compensation module, and finally reaches the human eye, so as to allow the human eye to gaze at the luminous LED bead to achieve sight fixation; the light beam exiting from the beam scanning module is transmitted through the first dichroic beam splitter of the sight beacon module, and then enters the defocus compensation module to continue to propagate.

The pupil monitoring module is configured to comprise a ring-shaped LED array, a second dichroic beam splitter, an imaging lens and an area-array detector, wherein the light emitted by the ring-shaped LED array illuminates the pupil of the human eye, and is reflected by the pupil of the human eye, passes through a hollow part of the ring-shaped LED array, is reflected by the second dichroic beam splitter, and is focused by the imaging lens to the area-array detector, the area-array detector is configured to convert light signal into an electrical signal and then output the electrical signal to the control module; the control module is configured to obtain a pupil imaging image and finally output the pupil imaging image to the output module for display and storage.

Preferably, the control module is configured to control the first scanning mirror and the second scanning mirror in the beam scanning module by outputting a voltage signal to carry out different scanning imaging functions;

wherein, the large field-of-view imaging function is performed by the following process:
the adaptive optics module is in a shutdown state or a non-working power-on state;
the first scanning mirror performs the transverse scanning of the retinal plane under the driving of a periodic voltage signal; the second scanning mirror performs the vertical scanning of the retinal plane under the driving of a periodic voltage signal; the retinal scanning angles of the first scanning mirror and the second scanning mirror driven by periodic voltage signals are no less than 20 degrees;
the detection module converts the acquired light signal of the fundus retina into an electrical signal, the control module synchronizes the periodic driving voltage signals of the first scanning mirror and the second scanning mirror, and the control module samples the electrical signal to reconstruct an imaging image of the retina with a large field of view which is then output to the output module for display and storage;
wherein, the small field-of-view high-resolution imaging function is performed by the following process:
the adaptive optics module is in a power-on working state to measure and correct wavefront aberration;
the first scanning mirror performs the transverse scanning of the retinal plane under the driving of a periodic voltage signal; the second scanning mirror generates a certain transverse and vertical inclination angle under the driving of a DC voltage signal for locating the light beam illuminating the fundus retina at a position of interest, and then is driven by a periodic voltage signal to perform the vertical scanning of the retinal plane; the retinal scanning angles of the first scanning mirror and the second scanning mirror driven by periodic voltage signals are no greater than 5 degrees;
the DC voltage signal is calculated by the control module according to a fundus retinal coordinate position;
the detection module converts the acquired light signal of the fundus retina into an electrical signal, the control module synchronizes the periodic driving voltage signals of the first scanning mirror and the second scanning mirror, and the control module samples the electrical signal to reconstruct an imaging image of the retina with a small field of view and high resolution and at the same time marks the fundus retinal coordinate position in the imaging image; the imaging image of the retina with a small field of view and high resolution is output by the control module to the output module for display and storage;
wherein, the large field-of-view high-resolution imaging function is performed by the following process:
the adaptive optics module is in a power-on working state to measure and correct wavefront aberration;
the first scanning mirror performs the transverse scanning of the retinal plane under the driving of a periodic voltage signal; the second scanning mirror performs the vertical scanning of the retinal plane under the driving of a periodic voltage signal; the retinal scanning angles of the first scanning mirror and the second scanning mirror driven by periodic voltage signals are no greater than 5 degrees;
at this time, the second scanning mirror generates a certain transverse and vertical inclination angle under the driving of a DC voltage signal to tilt the light beam to sequentially illuminate each area of the fundus retina; a single-time transverse and vertical inclination angle of the second scanning mirror is no greater than 3 degrees, a maximum retinal transverse and longitudinal inclination angle of the second scanning mirror driven by a DC voltage signal is no greater than 15 degrees; the DC voltage signal is calculated by the control module according to a fundus retinal coordinate position;
when each area of the fundus retina is sequentially illuminated by the light beam, the control module can obtain high-resolution imaging images of each area of the retina, and the control module stitches the high-resolution imaging images according to the fundus retinal coordinate positions of the high-resolution imaging images of the respective areas to obtain an image of the fundus retina with a large field of view and high resolution which is then output to the output module for display and storage.

Preferably, the light source module includes a plurality of light sources, wherein the lights emitted from the plurality of light sources are coupled by an optical-fiber coupler and go into a collimator to be collimated into a parallel light beam, or wherein the lights emitted from the plurality of light sources are collimated by corresponding collimators respectively into parallel light beams which are then coupled by a dichroic beam splitter to enter the optical path;

the collimator is a single lens, an achromatic lens, an apochromatic lens or a parabolic reflector for collimating the light beam emitted by the light source into a parallel light beam;

the first beam splitter is a broadband beam splitter, wherein 20% of the parallel light beam exiting from the collimator is transmitted through the beam splitter and continues to propagate into the adaptive optics module, and 80% of the returning imaging light beam exiting from the adaptive optics module is reflected by the first beam splitter to enter the detection module.

Preferably, the wavefront sensor included in the adaptive optics module is one of a microprism array Hartmann wavefront sensor, a microlens array Hartmann wavefront sensor, a quadrangular pyramid sensor and a curvature sensor, and the wavefront corrector is one of a deformable reflection mirror, a liquid crystal spatial light modulator, a micromachined membrane deformable mirror, a micro-electromechanical deformable mirror, a dual piezoelectric ceramic deformable mirror and a liquid deformable mirror;

95% of the parallel light beam output by the light source module is transmitted through the second beam splitter to the wavefront corrector; the returning imaging light beam is reflected by the wavefront corrector to the second beam splitter, wherein 5% of the light energy of the returning imaging light beam is reflected by the second beam splitter into the wavefront sensor for measuring wavefront aberration, and the remaining 95% of the light energy of the returning imaging light beam is transmitted through the second beam splitter to the first beam splitter to continue to propagate.

A large field-of-view adaptive optics retinal imaging method with common optical path beam scanning, which employs the system described above for imaging, comprises the following steps:

Step S1: turning on and starting the system;

Step S2: placing the subject's head on a headrest bracket, turning on the pupil monitoring module, and manually adjusting the headrest bracket or using the control module to automatically adjust the headrest bracket to translate in three-dimensional way, so that the pupil is imaged in a central area of the field of view;

Step S3: manually sliding the flat-field objective lens along the central optical axis thereof, or using the control module to drive a motor to move the position of the flat-field objective lens on the guide rail, so as to compensate and correct refractive error of the human eye;

Step S4: lighting one LED bead of an LED array in the sight beacon module, so as to allow the subject to gaze at the light spot to achieve sight fixation;

Step S5: switching the adaptive optics module into a shutdown state or a non-working power-on state, setting the beam scanning module to the large field-of-view scanning mode, and using the control module to control the beam scanning module to perform large field-of-view scanning to obtain a large field-of-view imaging image of the retina which is output to the output module;

Step S6: switching the adaptive optics module into a power-on working state to measure and correct wavefront aberration, and using the control module to control the beam scanning module to perform small field-of-view scanning which includes two small field-of-view scanning modes S61 and S62;

Step S61: using the control module to control the beam scanning module to obtain a small field-of-view high-resolution imaging image which is output to the output module;

Step S62: using the control module to control the beam scanning module to obtain a large field-of-view high-resolution imaging image which is output to the output module;

wherein the sequence of Step 55 and Step S6 can be reversed, and Step S61 and Step S62 are selectable to be performed without a particular sequential relation.

The beneficial effects of the present application are as follows:

The present application proposes a large field-of-view adaptive optics retinal imaging system and method with common optical path beam scanning. The system of the present application uses two scanning mirrors to form a common optical path beam scanning structure, wherein the first scanning mirror performs transverse scanning of the retina, the second scanning mirror performs vertical scanning of the retina, and at the same time, the second scanning mirror can also perform horizontal and vertical tilt under the driving of a DC voltage, so as to locate the illumination light beam to an area of interest on the retina. By controlling the two scanning mirrors to be in different scanning modes, different scanning imaging functions can be carried out, including a large field-of-view scanning imaging function which can acquire a large field-of-view imaging image of the retina; a small field-of-view high-resolution imaging function which can observe a small field-of-view high-resolution imaging image at any position of interest on the retina; and a large field-of-view high-resolution imaging function which can stitch the high-resolution imaging images according to the fundus retinal coordinate positions of the high-resolution imaging images of the respective areas to obtain an image of the fundus retina with a large field of view and high resolution.

The present application provides a large field-of-view adaptive optics retinal imaging system and method with common optical path beam scanning, which can acquire a large field-of-view imaging image of the fundus retina, a small field-of-view high-resolution imaging image for any area of interest and a large field-of-view high-resolution imaging image, and the three types of imaging images are acquired by the common optical path structure, so the characteristics of the three types of imaging images have good consistency, which is convenient for processing and operation. At the same time, the system is simple in structure, and the common optical path structure can obtain three types of retinal imaging images, and by switching between different synchronous scanning modes, it can not only observe lesion distribution areas of retinal disease by large field-of-view imaging, but also observe fine structures of a particular lesion area by small field-of-view high-resolution imaging. Large field-of-view imaging images can be used to observe characteristics of the structure and lesions of the retina in a wide range over the retina, small field-of-view high-resolution imaging images can be used to observe fine structures of any area of interest, and large field-of-view high-resolution imaging images can be used to observe fine structures of the retina in a wide range. Multiple types of imaging images are acquired by common optical path beam scanning, which meets the requirements of different application scenarios and greatly improves the application range of retinal imaging.

REFERENCE NUMERALS

1—light source module; 2—adaptive optics module; 3—beam scanning module; 4—defocus compensation module; 5—human eye; 6—sight beacon module; 7—pupil monitoring module; 8—detection module; 9—control module; 10—output module; 101—light source; 102—collimator; 103—first beam splitter; 201—second beam splitter; 202—wavefront corrector; 203—transmissive or reflective telescope; 204—wavefront sensor; 301—first scanning mirror; 302—transmissive or reflective telescope; 303—second scanning mirror; 401—scanning objective lens; 402—flat-field objective lens; 403—guide rail; 601—LED array; 602—lens; 603—first dichroic beam splitter; 701—ring-shaped LED array; 702—second dichroic beam splitter; 703—imaging lens; 704—area-array detector; 801—collection lens; 802—confocal pinhole; 803—high sensitivity detector.

DETAILED DESCRIPTION

The present application will be further described in detail in conjunction with the embodiments below, so that a person skilled in the art can implement it with reference to the text of the description.

It should be understood that the terms such as "having", "including", and "comprising" used herein do not exclude the presence or addition of one or more other elements or combinations thereof.

Figure 1:
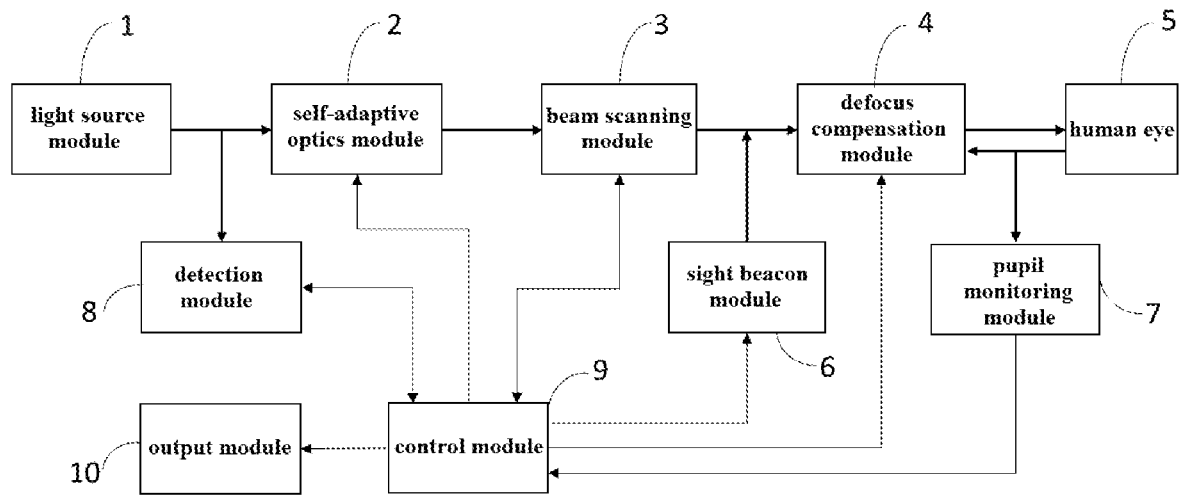
FIG. 1 is a schematic block diagram of a large field-of-view adaptive optics retinal imaging system with common optical path beam scanning according to the present application.
Figure 2:
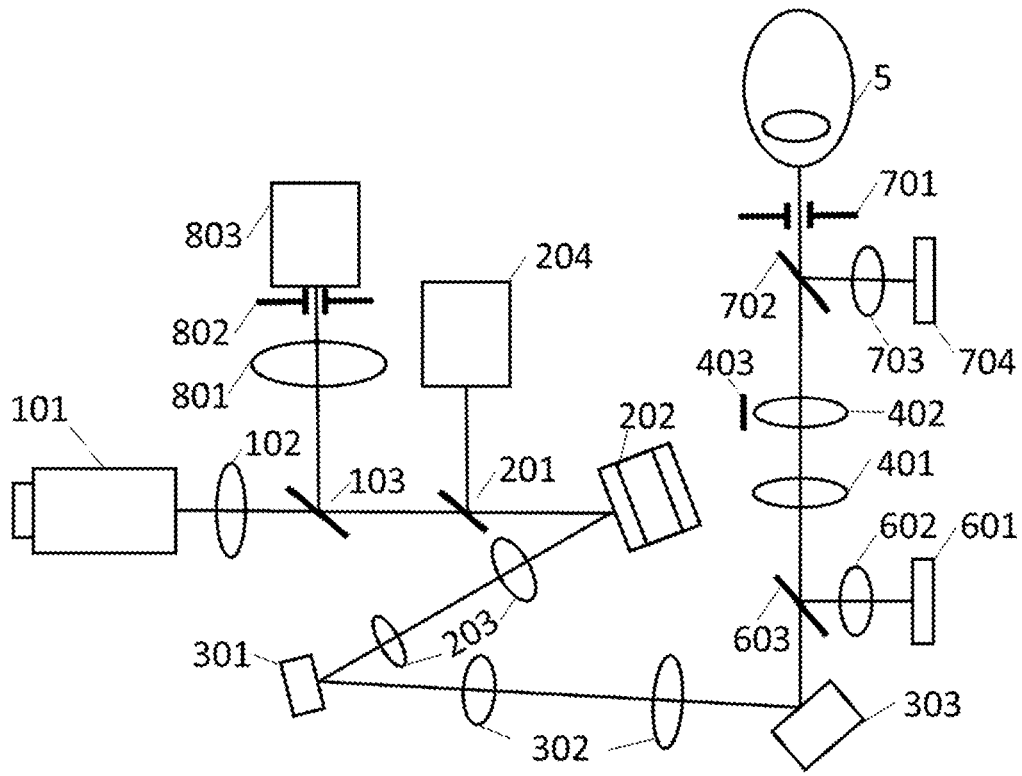
FIG. 2 is a schematic diagram of an optical path structure of a large field-of-view adaptive optics retinal imaging system with common optical path beam scanning according to the present application.

As shown in FIGS. 1-2, a large field-of-view adaptive optics retinal imaging system with common optical path beam scanning in the present embodiment comprises: a light source module 1, an adaptive optics module 2, a beam scanning module 3, a defocus compensation module 4, a sight beacon module 6, a pupil monitoring module 7, a detection module 8, a control module 9 and an output module 10;

the light source module 1 is configured to emit a parallel light beam, wherein the parallel light beam irradiates a human eye 5 after sequentially going through the adaptive optics module 2, the beam scanning module 3 and the defocus compensation module 4, imaging light that is scattered by the human eye 5 and carries aberration information of the human eye and light intensity information returns along an original optical path of the parallel light beam and reaches the adaptive optics module 2 and the detection module 8;

the adaptive optics module 2 is configured to receive the imaging light carrying the aberration information of the human eye, and perform real-time measurement and correction of aberration of the human eye;

the beam scanning module 3 is controlled by the control module 9, and the beam scanning module is configured in different scanning modes for carrying out different scanning imaging functions at least including a large field-of-view imaging function, a small field-of-view high-resolution imaging function and a large field-of-view high-resolution imaging function;

the defocus compensation module 4 is configured to achieve compensation of refractive error of the human eye;

the sight beacon module 6 is configured to guide and fix a sight beacon in different areas of a retina of the human eye;

the pupil monitoring module 7 is configured to align and monitor a pupil of the human eye;

the detection module 8 is configured to acquire the returning imaging light of the human eye, convert the imaging light into an electrical signal, and transmit the electrical signal to the control module 9; and the output module 10 is configured to connect to the control module 9, and display and store imaging images of the human eye (fundus retinal imaging images and pupil imaging images).

The light source module 1, the adaptive optics module 2, the beam scanning module 3, the sight beacon module 6, the defocus compensation module 4 and the pupil monitoring module 7 are sequentially arranged along an incident optical path; the light source module 1 is configured to comprise a light source 101, a collimator 102 and a first beam splitter 103 that are sequentially arranged along the incident optical path, and is configured to output a parallel light beam to the adaptive optics module 2, wherein the light emitted by the light source 101 passes through the collimator 102, and is then partially transmitted through the first beam splitter 103 to enter the adaptive optics module 2.

The light source module 1 may include a plurality of light sources 101, wherein the lights emitted from the plurality of light sources 101 may be coupled by an optical-fiber coupler and go into the collimator 102 to be collimated into a parallel light beam, or wherein the lights emitted from the plurality of light sources 101 may be collimated by corresponding collimators 102 respectively into parallel light beams which are then coupled by a dichroic beam splitter to enter the optical path; the plurality of light sources 101 may include typical fundus imaging illumination wavelengths, such as 488 nm, 515 nm, 650 nm, 680 nm, 780 nm, 830 nm and other characteristic wavelengths.

The collimator 102 may be a single lens, an achromatic lens, an apochromatic lens or a parabolic reflector for collimating the light beam emitted by the light source 101 into a parallel light beam. In this embodiment, the reflection collimator 102RC12FC-P01 of the Thorlabs Corporation is selected.

In this embodiment, the first beam splitter 103 is a broadband beam splitter, and its ratio of transmission to reflection is 20:80. 20% of the parallel light beam exiting from the collimator 102 is transmitted through the first beam splitter 103 and continues to propagate into the adaptive optics module 2, and 80% of the returning imaging light beam exiting from the adaptive optics module 2 is reflected by the first beam splitter 103 to enter the detection module 8.

The first dichroic beam splitter 603 has a transmission effect on all wavelengths included in the light source 101, and the second dichroic beam splitter 702 has a transmission effect on all wavelengths included in the light source 101.

The adaptive optics module 2 is configured to comprise a second beam splitter 201, a wavefront corrector 202, a transmissive or reflective telescope 203 and a wavefront sensor 204 that are sequentially arranged along the incident optical path, and is configured to connect to the beam scanning module 3, detect and correct wavefront aberration; the parallel light beam output by the light source module 1, after partially being transmitted through the second beam splitter 201, is reflected to the transmissive or reflective telescope 203 by the wavefront corrector 202 to enter the beam scanning module 3; the returning imaging light carrying the aberration information of the human eye and the light intensity information exits from the beam scanning module 3 and enters the transmissive or reflective telescope 203, and then is reflected to the second beam splitter 201 by the wavefront corrector 202; part of the imaging light is reflected to the wavefront sensor 204 by the second beam splitter 201 to realize measurement of wavefront aberration, and the rest of the imaging light is transmitted through the second beam splitter 201 to continue to propagate;

the wavefront aberration detected by the wavefront sensor 204 is processed by the control module 9 to obtain a wavefront control voltage which is output to the wavefront corrector 202, so as to realize correction of wavefront aberration.

The wavefront sensor 204 included in the adaptive optics module 2 is one of a microprism array Hartmann wavefront sensor, a microlens array Hartman wavefront sensor, a quadrangular pyramid sensor and a curvature sensor, and the wavefront corrector 202 is one of a deformable reflection mirror, a liquid crystal spatial light modulator, a micromachined membrane deformable mirror, a micro-electromechanical deformable mirror, a dual piezoelectric ceramic deformable mirror and a liquid deformable mirror.

In this embodiment, the second beam splitter 201 is a broadband beam splitter, and its ratio of transmission to reflection is 95:5. 95% of the parallel light beam output by the light source module 1 is transmitted through the second beam splitter 201 to the wavefront corrector 202; the returning imaging light beam is reflected by the wavefront corrector 202 to the second beam splitter 201, wherein 5% of the light energy of the returning imaging light beam is reflected by the second beam splitter into the wavefront sensor 204 for measuring wavefront aberration, and the remaining 95% of the light energy of the returning imaging light beam is transmitted through the second beam splitter to the first beam splitter 103 to continue to propagate.

The detection module 8 is configured to comprise a collection lens 801, a confocal pinhole 802 and a high sensitivity detector 803, wherein the part of the returning imaging light that is transmitted through the second beam splitter 201 of the adaptive optics module 2 reaches the first beam splitter 103, and is partially reflected by the first beam splitter 103 to the collection lens 801, focused by the collection lens 801 and then passes through the confocal pinhole 802 to reach the high sensitivity detector 803, a photoelectric conversion is performed by the high sensitivity detector 803 to obtain an electrical signal, then the electrical signal is output to the control module 9 for processing to obtain a retinal imaging image, and finally the retinal imaging image is output to the output module 10 for display and storage; the confocal pinhole 802 is disposed at a focal point of the collection lens 801.

The collection lens 801 may be an achromatic lens, an apochromatic lens or a lens combination with a focal length of no less than 100 mm. In a preferred embodiment, the confocal pinhole 802 has a size of 50 microns, which can also be changed according to the light energy efficiency while not exceeding 200 microns. The high sensitivity detector 803 may be a photomultiplier tube or an avalanche photodiode.

The beam scanning module 3 is configured to comprise a first scanning mirror 301 and a second scanning mirror 303, and the two scanning mirrors are connected through a transmissive or reflective telescope 302 to achieve pupil plane matching; the first scanning mirror 301 is configured to perform transverse scanning of the retinal plane, the second scanning mirror 303 is configured to perform vertical scanning of the retinal plane under the driving of a periodic voltage, the second scanning mirror 303 is able to generate a certain transverse and vertical inclination angle under the driving of a DC voltage, the second scanning mirror 303 is also able to perform transverse and vertical two-dimensional scanning of the retinal plane under the driving of a periodic voltage at the same time of generating the transverse and vertical inclination angle under the driving of a DC voltage;

the first scanning mirror 301 and the second scanning mirror 302 can have their front and rear positions interchanged without affecting the imaging effect;

the beam scanning module 3 is controlled by a voltage signal output from the control module 9 and is configurable in different scanning modes for carrying out different imaging functions including a large field-of-view imaging function, a small field-of-view high-resolution imaging function and a large field-of-view high-resolution imaging function.

In the embodiment, the first scanning mirror 301 is a resonance mirror 6SC08KA040-02Y of the Cambrige Corporation, and the second scanning mirror 303 is a fast-steering mirror MR-30-15-G-25×25D of the Optotune Corporation.

The defocus compensation module 4 is configured to comprise a scanning objective lens 401, a flat-field objective lens 402 and a guide rail 403 that are sequentially arranged along the incident optical path, the light beam exiting from the beam scanning module 3 propagates to the pupil monitoring module 7 through the defocus compensation module 4, and the flat-field objective lens 402 can reciprocate along the central axis of the flat-field objective lens 402 on the guide rail 403 to achieve the compensation of refractive error of the human eye.

The extending direction of the guide rail 403 is consistent with the direction of the central axis of the flat-field objective lens 402, and the flat-field objective lens 402 is slidably disposed on the guide rail 403.

In a preferred embodiment, the flat-field objective lens 402 is configured to connect to the guide rail 403 through a motor, and the flat-field objective lens 402 is controlled via the control module 9 to reciprocate along the central axis of the flat-field objective lens 402, so as to achieve the compensation of refractive error of the human eye. Further preferably, the scanning objective lens 401 is an achromatic lens, an apochromatic lens, an aspheric lens or a lens combination with a field-of-view angle of greater than 30 degrees. The flat-field objective lens 402 may be an achromatic lens, an apochromatic lens, an aspheric lens or a lens combination to achieve a flat-field effect on the fundus retina.

The sight beacon module 6 is configured to comprise an LED array 601, a lens 602 and a first dichroic beam splitter 603, wherein the light emitted by any one of LED beads in the LED array 601 after being lit by the control module 9 propagates through the lens 602, is reflected by the first dichroic mirror 603 to enter the defocus compensation module 4, and finally reaches the human eye 5, so as to allow the human eye 5 to gaze at the luminous LED bead to achieve sight fixation; the light beam exiting from the beam scanning module 3 is transmitted through the first dichroic beam splitter 603 of the sight beacon module 6, and then enters the defocus compensation module 4 to continue to propagate.

The LED beads of the LED array 601 have a certain characteristic wavelength selected in the range of 500 nm-600 nm. The wavelength selected for the LED array 601 and the wavelength contained in the light source 101 cannot be the same, and must have a wavelength difference of more than 30 nm to ensure that the first dichroic beam splitter 603 has a reflection effect on the wavelength selected for the LED array 601 and has a transmission effect on the wavelength selected for the light source 101. By the control module 9 lighting the LED beads at different positions on the LED array 601, different areas of the fundus retina would be guided to be imaging areas.

The pupil monitoring module 7 is configured to comprise a ring-shaped LED array 701, a second dichroic beam splitter 702, an imaging lens 703 and an area-array detector 704, wherein the light emitted by the ring-shaped LED array 701 illuminates the pupil of the human eye 5, and is reflected by the pupil of the human eye 5, passes through a hollow part of the ring-shaped LED array 701, is reflected by the second dichroic beam splitter 702, and is focused by the imaging lens 703 to the area-array detector 704, the area-array detector 704 is configured to convert light signal into an electrical signal and then output the electrical signal to the control module 9; the control module 9 is configured to obtain a pupil imaging image and finally output the pupil imaging image to the output module 10 for display and storage.

The LED beads of the ring-shaped LED array 701 may have a near-infrared wavelength selected to be 900 nm or above, and the second dichroic beam splitter 702 has a reflection effect on the emission wavelength of the LED beads of the ring-shaped LED array 701.

There are multiple processes in the operation of the imaging system, including a main optical path transmission process, subject-related processes, an adaptive optics aberration measurement and correction process, and scanning imaging processes.

1. Main Optical Path Transmission Process

The transmission optical path is as follows: the light emitted by the light source 101, approximately regarded as a point light source 101, is collimated by the collimator 102 into a parallel light beam, and is split by the first beam splitter 103, so that 20% of the parallel light beam is transmitted through the first beam splitter 103 to enter the second beam splitter 201 for light splitting; 95% of the incident light reaching the second beam splitter 201 is transmitted through the second beam splitter 201 and then is reflected by the wavefront corrector 202, and the parallel light beam continues to pass through the transmissive or reflective telescope 203 to achieve pupil aperture matching, and after being reflected by the first scanning mirror 301, the pupil aperture diameter thereof is matched by the transmissive or reflective telescope 302, and then the light beam is reflected by the second scanning mirror 303, is transmitted through the first dichroic beam splitter 603, sequentially passes through the scanning objective lens 401 and the flat-field objective lens 402, and then is transmitted through the second dichroic beam splitter 702 and passes through a hollow part of the ring-shaped LED array 701 to reach the human eye 5, and the light beam is focused to a point on the fundus retina by the optical system of the human eye 5;

The fundus of the human eye has a scattering effect on the incident light. The scattered imaging light carries the aberration information of the human eye and the light intensity information at this point on the fundus, and returns to the second beam splitter 201 along the original path. The scattered light is split by the second beam splitter 201 again, so that 5% of the light energy is reflected by the second beam splitter 201 into the wavefront sensor 204, and the remaining 95% of the light energy is transmitted through the second beam splitter 201 to propagate to the first beam splitter 103. 80% of the light reaching the first beam splitter 103 is reflected by the first beam splitter 103 into the collection lens 801, passes through the confocal pinhole 802, and reaches the high sensitivity detector 803. The high sensitivity detector 803 performs photoelectric conversion to obtain an electrical signal, which is then output to the control module 9 for processing. After processing, a retinal imaging image is obtained and finally output to the output module 10 for display and storage.

2. Subject-Related Processes

The subject-related processes mainly include alignment and monitoring of pupil, compensation and correction of refractive error, guidance and fixation of a sight beacon.

(1) Alignment and Monitoring of Pupil

The pupil monitoring module 7 comprises a ring-shaped LED array 701, a second dichroic beam splitter 702, an imaging lens 703 and an area-array detector 704, wherein the ring-shaped LED array 701 includes at least three LED beads which are arranged along a ring at equal intervals, and the light-transmitting aperture of the hollow part thereof is no less than the diameter of the imaging light beam. The light emitted by the ring-shaped LED array 701 illuminates the pupil of the human eye 5, and is reflected by the pupil of the human eye 5, passes through the hollow part of the ring-shaped LED array 701, is reflected by the second dichroic beam splitter 702, and is focused by the imaging lens 703 to the area-array detector 704, the area-array detector 704 is configured to convert light signal into an electrical signal and then output the electrical signal to the control module 9; the control module is configured to obtain a pupil imaging image and finally output the pupil imaging image to the output module 10 for performing functions such as display, storage, processing.

When the system of the present application is working, the subject's head is placed on a headrest bracket. The headrest bracket has a three-dimensional translation adjustment function. The three-dimensional translatable guide rail of the headrest bracket can be manually adjusted, or the three-dimensional translatable guide rail of the headrest bracket can be configured to be driven by a motor which is driven by the control module 9 to realize automatic adjustment, so that the pupil is imaged in a central area of the field of view.

(2) Compensation and Correction of Refractive Error

The defocus compensation module 4 comprises a scanning objective lens 401, a flat-field objective lens 402 and a guide rail 403. The extending direction of the guide rail 403 is consistent with the direction of the central axis of the flat-field objective lens 402, and the flat-field objective lens 402 is slidably disposed on the guide rail 403. After the incident light exits from the beam scanning module 3, it passes through the scanning objective lens 401 and the flat-field objective lens 402 sequentially, and the flat field objective lens 402 is controlled by the control module 9 to reciprocate along the central axis of the flat-field objective lens to achieve the compensation of refractive error of the human eye.

(3) Guidance and Fixation of a Sight Beacon

The sight beacon module 6 comprises an LED array 601, a lens 602 and a first dichroic beam splitter 603. One LED bead in the LED array 601 is lit by the control module 9, and the light emitted by the LED bead reaches the first dichroic beam splitter 603 after passing through the lens 602, and is reflected by the first dichroic beam splitter 603 toward the flat-field objective lens 402 to propagate by passing through the scanning objective lens 401, the flat-field objective lens 402 and the second dichroic beam splitter 702 sequentially, and then passes through the hollow part of the ring-shaped LED array 701, reaches the human eye, and is focused on the fundus retina by the optical system of the human eye.

The human eye looks at the LED light emitting point to achieve sight fixation.

By the control module 9 lighting the LED beads at different positions on the LED array 601, different areas of the fundus retina will be guided to be imaging areas.

3. Adaptive Optics Aberration Measurement and Correction Process

The returning imaging light carrying the aberration information of the human eye and the light intensity information exits from the beam scanning module 3 and enters the transmissive or reflective telescope 203, and then is reflected to the second beam splitter 201 by the wavefront corrector 202; part of the imaging light is reflected to the wavefront sensor 204 by the second beam splitter 201 to realize measurement of wavefront aberration, and the rest of the imaging light is transmitted through the second beam splitter 201 to continue to propagate; the wavefront sensor 204 is configured to receive an imaging light beam containing the aberration information of the human eye and transmit the aberration information to the control module 9, and the control module 9 is configured to perform wavefront calculation, obtain a wavefront correction voltage and output the wavefront correction voltage to the wavefront corrector 202, and the wavefront corrector 202 is configured to correct aberration of the human eye in real time.

4. Scanning Imaging Processes

The beam scanning module 3 comprises a first scanning mirror 301 and a second scanning mirror 303, and the two scanning mirrors are connected through a transmissive or a reflective telescope 302 to achieve pupil plane matching. The first scanning mirror 301 and the second scanning mirror 303 can have their front and rear positions interchanged without affecting the imaging effect. The first scanning mirror 301 and the second scanning mirror 303 are controlled by voltage signals output from the control module 9 and are configurable in different scanning modes for carrying out different imaging functions.

(1) The large field-of-view imaging function is performed by the following process:

the adaptive optics module 2 is in a shutdown state or a non-working power-on state;

the first scanning mirror 301 performs the transverse scanning of the retinal plane under the driving of a periodic voltage signal; the second scanning mirror 303 performs the vertical scanning of the retinal plane under the driving of a periodic voltage signal. The retinal scanning angles of the first scanning mirror 301 and the second scanning mirror 303 driven by periodic voltage signals are no less than 20 degrees;

the detection module 8 converts the acquired light signal of the fundus retina into an electrical signal, the control module 9 synchronizes the periodic driving voltage signals of the first scanning mirror 301 and the second scanning mirror 303, and the control module 9 samples the electrical signal to reconstruct an imaging image of the retina with a large field of view which is then output to the output module 10 for performing functions such as display, storage, processing.

(2) The small field-of-view high-resolution imaging function is performed by the following process:

the adaptive optics module 2 is in a power-on working state to measure and correct wavefront aberration;

the first scanning mirror 301 performs the transverse scanning of the retinal plane under the driving of a periodic voltage signal; the second scanning mirror 303 generates a certain transverse and vertical inclination angle under the driving of a DC voltage signal for locating the light beam illuminating the fundus retina at a position of interest, and then is driven by a periodic voltage signal to perform the vertical scanning of the retinal plane; the retinal scanning angles of the first scanning mirror 301 and the second scanning mirror 303 driven by periodic voltage signals are no greater than 5 degrees;

the DC voltage signal is calculated by the control module 9 according to a fundus retinal coordinate position;

the detection module 8 converts the acquired light signal of the fundus retina into an electrical signal, the control module 9 synchronizes the periodic driving voltage signals of the first scanning mirror 301 and the second scanning mirror 303, and the control module 9 samples the electrical signal to reconstruct an imaging image of the retina with a small field of view and high resolution and at the same time marks the fundus retinal coordinate position in the imaging image; the imaging image of the retina with a small field of view and high resolution is output by the control module 9 to the output module 10 for performing functions such as display, storage, processing.

(3) The large field-of-view high-resolution imaging function is performed by the following process:

the adaptive optics module 2 is in a power-on working state to measure and correct wavefront aberration;

the first scanning mirror 301 performs the transverse scanning of the retinal plane under the driving of a periodic voltage signal; the second scanning mirror 303 performs the vertical scanning of the retinal plane under the driving of a periodic voltage signal; the retinal scanning angles of the first scanning mirror 301 and the second scanning mirror 303 driven by periodic voltage signals are no greater than 5 degrees;

at this time, the second scanning mirror 303 generates a certain transverse and vertical inclination angle under the driving of a DC voltage signal to tilt the light beam to sequentially illuminate each area of the fundus retina; a single-time transverse and vertical inclination angle of the second scanning mirror 303 is no greater than 3 degrees, a maximum retinal transverse and longitudinal inclination angle of the second scanning mirror 303 driven by a DC voltage signal is no greater than 15 degrees; the DC voltage signal is calculated by the control module 9 according to a fundus retinal coordinate position;

when each area of the fundus retina is sequentially illuminated by the light beam, the control module 9 can obtain high-resolution imaging images of each area of the retina, and the control module 9 stitches the high-resolution imaging images according to the fundus retinal coordinate positions of the high-resolution imaging images of the respective areas to obtain an image of the fundus retina with a large field of view and high resolution which is then output to the output module 10 for performing functions such as display, storage, processing.

Figure 3:
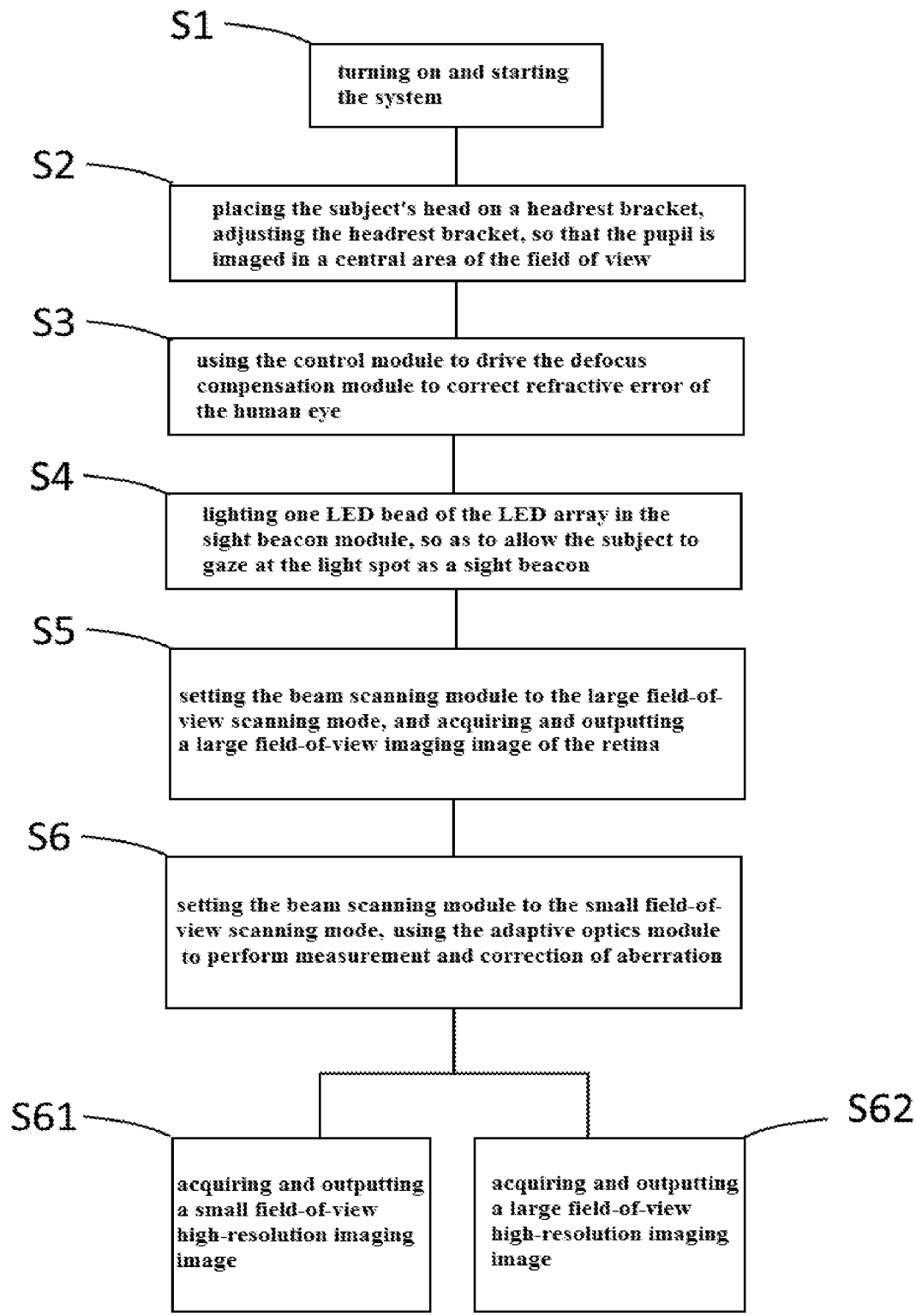
FIG. 3 is a flow chart of a large field-of-view adaptive optics retinal imaging system with common optical path beam scanning according to the present application.

As shown in FIG. 3, the present application also provides a large field-of-view adaptive optics retinal imaging method with common optical path beam scanning, the method employs the above system for imaging, and comprises the following steps:

Step S1: turning on and starting the system;

Step S2: placing the subject's head on a headrest bracket, turning on the pupil monitoring module 7, and manually adjusting the headrest bracket or using the control module 9 to automatically adjust the headrest bracket to translate in three-dimensional way, so that the pupil is imaged in a central area of the field of view;

Step S3: manually sliding the flat-field objective lens 402 along the central optical axis thereof, or using the control module 9 to drive a motor to move the position of the flat-field objective lens 402 on the guide rail 403, so as to compensate and correct refractive error of the human eye;

Step S4: lighting one LED bead of an LED array 601 in the sight beacon module, so as to allow the subject to gaze at the light spot to achieve sight fixation;

Step S5: switching the adaptive optics module 2 into a shutdown state or a non-working power-on state, setting the beam scanning module 3 to the large field-of-view scanning mode, and using the control module 9 to control the beam scanning module 3 to perform large field-of-view scanning to obtain a large field-of-view imaging image of the retina which is output to the output module 10;

Step S6: switching the adaptive optics module 2 into a power-on working state to measure and correct wavefront aberration, and using the control module 9 to control the beam scanning module 3 to perform small field-of-view scanning;

Step S61: using the control module 9 to control the beam scanning module 3 to obtain a small field-of-view high-resolution imaging image which is output to the output module 10;

Step S62: using the control module 9 to control the beam scanning module 3 to obtain a large field-of-view high-resolution imaging image which is output to the output module 10.

Wherein the sequence of Step 55 and Step S6 can be reversed.

After the operation of Step S6 is completed, Step S61 and Step S62 are selectable to be performed according to actual needs.

It is well known that, the existing laser confocal scanning ophthalmoscopes having a large field of view of imaging do not have sufficient resolution to observe fine structures of the retina; and the existing laser confocal scanning ophthalmoscopes combined with adaptive optics can observe fine structures of the retina, but have a small field of view of imaging which makes it impossible to observe lesions in a larger field of view.

As compared with the technical achievements in the field of laser confocal scanning imaging at home and abroad, the present application proposes a large field-of-view adaptive optics retinal imaging system with common optical path beam scanning based on the basic principles of a combination of adaptive optics and confocal scanning technology, wherein two scanning mirrors are used to form a common optical path structure, the two scanning mirrors are configured in different scanning modes, which can perform large field-of-view imaging of more than 20 degrees on the retina for observing lesion distribution areas of retinal disease, and can also perform small field-of-view imaging of no more than 5 degrees on the retina, and with correction of aberration by adaptive optics, small field-of-view high-resolution imaging can be realized to observe fine structures and pathological changes of the lesion, and a second scanning mirror 302 is further configured to perform sequential tilted illumination of the light beam in each area of the retina, and then, by image stitching, a large field-of-view high-resolution imaging of the retina over 15 degrees can be acquired at one time.

The present application proposes a large field-of-view adaptive optics retinal imaging system with common optical path beam scanning. The system of the present application uses two scanning mirrors to form a common optical path beam scanning structure, wherein the first scanning mirror 301 performs transverse scanning of the retina, the second scanning mirror 303 performs vertical scanning of the retina, and at the same time, the second scanning mirror 303 can also perform horizontal and vertical tilting under the driving of a DC voltage, so as to locate the illumination light beam to the area of interest on the retina.

By controlling the two scanning mirrors to be in different scanning modes, different scanning imaging functions can be carried out.

(1) Large Field-of-View Scanning Imaging

The first scanning mirror 301 is configured for transverse scanning, and the second scanning mirror 303 is configured for vertical scanning. The retinal scanning angles of the two scanning mirrors are no less than 20 degrees. At this time, the adaptive optics correction function is turned off to be in a shutdown state or a non-working power-on state, and a retinal imaging image with a large field of view is obtained.

(2) Small Field-of-View High-Resolution Imaging

The first scanning mirror 301 is configured for transverse scanning, and the second scanning mirror 303 is configured for vertical scanning. The retinal scanning angles of the two scanning mirrors are no greater than 5 degrees. At this time, the adaptive optics module performs the aberration measurement and correction function, so as to acquire a small field-of-view high-resolution imaging image of the retina with its aberration corrected. The second scanning mirror 303 can also generate a transverse and vertical inclination under the driving of a DC voltage signal for locating the light beam illuminating the fundus retina at a position of interest, so as to observe a small field-of-view high-resolution imaging image of any position of interest on the retina.

(3) Large Field-of-View High-Resolution Imaging

The first scanning mirror 301 is configured for transverse scanning, and the second scanning mirror 303 is configured for vertical scanning. The retinal scanning angles of the two scanning mirrors are no greater than 5 degrees. At this time, the adaptive optics module performs the aberration measurement and correction function, so as to acquire a small field-of-view high-resolution imaging image of the retina with its aberration corrected. The second scanning mirror 303 generates a transverse and vertical inclination angle under the driving of a DC voltage signal for locating the light beam illuminating the fundus retina at a position of interest, and the second scanning mirror 303 is configured to tilt the light beam to sequentially illuminate each area of the fundus retina, a single-time transverse and vertical inclination angle of the second scanning mirror 303 is no greater than 3 degrees, a maximum retinal transverse and longitudinal inclination angle of the second scanning mirror 303 driven by a DC voltage signal is no greater than 15 degrees.

When each area of the fundus retina is sequentially illuminated by the light beam, the control module can obtain high-resolution imaging images of each area of the retina, and the control module 9 stitches the high-resolution imaging images according to the fundus retinal coordinate positions of the high-resolution imaging images of the respective areas to obtain an image of the fundus retina with a large field of view and high resolution.

The present application provides a large field-of-view adaptive optics retinal imaging system and method with common optical path beam scanning, which can acquire a large field-of-view imaging image of the fundus retina, a small field-of-view high-resolution imaging image for any area of interest and a large field-of-view high-resolution imaging image, and the three types of imaging images are acquired by the common optical path structure, so the characteristics of the three types of imaging images have good consistency, which is convenient for processing and operation. At the same time, the system is simple in structure, and the common optical path structure can obtain three types of retinal imaging images, and by switching between different synchronous scanning modes, it can not only observe lesion distribution areas of retinal disease by large field-of-view imaging, but also observe fine structures of a particular lesion area by small field-of-view high-resolution imaging. Large field-of-view imaging images can be used to observe characteristics of the structure and lesions of the retina in a wide range over the retina, small field-of-view high-resolution imaging images can be used to observe fine structures of any area of interest, and large field-of-view high-resolution imaging images can be used to observe fine structures of the retina in a wide range. Multiple types of imaging images are acquired by common optical path beam scanning, which meets the requirements of different application scenarios and greatly improves the application range of retinal imaging.

Although the embodiments of the present application have been disclosed as above, they are not limited to the applications listed in the description and the embodiments. It can be fully applied to various fields suitable for the present application. For a person familiar with the art, additional modifications can be easily implemented, so the present application is not limited to specific details without departing from the general concept defined by the claims and the equivalent scope thereof.

The invention claimed is:

1. A large field-of-view adaptive optics retinal imaging system with common optical path beam scanning, characterized in that, the system comprises: a light source module, an adaptive optics module, a beam scanning module, a defocus compensation module, a sight beacon module, a pupil monitoring module, a detection module, a control module and an output module;

the light source module is configured to emit a parallel light beam, wherein the parallel light beam irradiates a human eye after sequentially going through the adaptive optics module, the beam scanning module and the defocus compensation module, imaging light that is scattered by the human eye and carries aberration information of the human eye and light intensity information returns along an original optical path of the parallel light beam and reaches the adaptive optics module and the detection module;

the adaptive optics module is configured to receive the imaging light carrying the aberration information of the human eye, and perform real-time measurement and correction of aberration of the human eye;

the beam scanning module is controlled by the control module, and the beam scanning module is configured in different scanning modes for carrying out different scanning imaging functions at least including a large field-of-view imaging function, a small field-of-view high-resolution imaging function and a large field-of-view high-resolution imaging function;

the defocus compensation module is configured to achieve compensation of refractive error of the human eye;

the sight beacon module is configured to guide and fix a sight beacon in different areas of a retina of the human eye;

the pupil monitoring module is configured to align and monitor a pupil of the human eye;

the detection module is configured to acquire the returning imaging light of the human eye, convert the imaging light into an electrical signal, and transmit the electrical signal to the control module; and the output module is configured to connect to the control module, and display and store imaging images of the human eye;

wherein the beam scanning module is configured to comprise a first scanning mirror and a second scanning mirror, and the two scanning mirrors are connected through a transmissive or reflective telescope to achieve pupil phane matching;

the first scanning mirror is configured to perform transverse scanning of the retinal plane, and the second scanning mirror is configured to perform vertical scanning of the retinal plane under the driving of a periodic voltage, in order to carry out the large field-of-view imaging function;

the second scanning mirror is configured to generate a certain transverse and vertical inclination angle under the driving of a DC voltage, the second scanning mirror is also configured to perform transverse and vertical two-dimensional scanning of the retinal plane under the driving of a periodic voltage at the same time of generating the transverse and vertical inclination angle under the driving of a DC voltage, in order to carry out the small field-of-view high-resolution imaging function and the large field-of-view high-resolution imaging function;

wherein the control miodule is configured to control the first scanning mirror and the second scanning miorror in the beam scanning module by outputting a voltage signal to carry out different scanning imaging functions;

wherein, the large field-of-view imaging function is performed by the following process:

the adaptive optics module is in a shutdown state or a non-working power-on state;

the first scanning mirror performs the transverse scanning of the retinal plane under the driving of a periodic voltage signal; the second scanning morror performs the vertical scanning of the retinal plane under the driving of a periodic voltage signal; the retinal scanning angles of the first scanning mirror and the second scanning mirror driven by periodic voltage signals are no less than 20 degrees;

the detection module converts the acquired light signal of the fundus retinal into an electrical signal, the control module synchronized the periodic driving voltage signals of the first scanning mirror and the second scanning mirror, and the control module samples the electrical signal to reconstruct an imaging image of the retina with a large field of view which is then output to the output module for display and storage;

wherein, the small field-of-view high-resolution imaging function is performed by the following process:

the adaptive optics module is in a power-on working state to measure and correct wavefront aberration;

the first scanning mirror performs the transverse scanning of the retinal plane under the driving of a periodic voltage signal; the second mirror generates a certain transverse and vertical inclination angle under the driving of a DC voltage signal for locating the light beam illuminating the fundus retina at a positioin of interest, and then is driven by a periodic voltage signal to perform the vertical scanning of the retinal plane; the retinal scanning angles of the first scanning mirror and the second scanning mirror driven by the periodic voltage signals are no greater than 5 degrees;

the DC voltage signal is calculated by the control module according to a fundus retinal coordinate position;

the detection module converts the acquired light signal of the fundus retina into an electrical signal, the control module synchronizes the periodic driving voltage signals of the first scanning mirror and the second scanning mirror, and the control module samples the electrical signal to reconstruct an imaging image of the retina with a small field of view and high resolution and at the same time marks the fundus retinal coordinate position in the imaging image; the imaging image of the retina with a small field of view and high resolution is output by the control module to the output module for display and storage;

wherein, the large field-of-ivew high-resolution imaging function is performed by the following process:

the adaptive optics module is in a power-on working state to measure and correct wavefront aberration;

the first scanning mirror performs the transverse scanning of the retinal plane under the driving of a periodic voltage signal; the second scanning mirror performs the vertical scanning of the retinal plane under the driving of a periodic voltage signal; the retinal scanning angles of the first scanning mirror and the second scanning mirror driven by periodic voltage signals are no greater that 5 degrees;

at this time, the second scanning mirror generates a certain transverse and vertical inclination angle under the driving of a DC voltage signal to tilt the light beam to sequentially illuminate each area of the fundus retina; a single-time transverse and vertical inclination angle of the second scanning mirror is no greater than 3 degrees, a maximum retinal transverse and longitudinal inclination angle of the second scanning mirror driven by a DC voltage signal is no greater that 15 degrees, the DC voltage signal is calculated by the control module according to a fundus retinal coordinate postion;

when each area of the fundus retina is sequentially illuminated by the light beam, the control module can obtain high-resolution imaging images of each area of the retina, and the control module stitches the high-resolution imaging images according to the fundus retinal coordinate positions of the high-resolution imaging images of the respective areas to obtain an image of the fundus retina with a large field of view and high resolution which is then output to the output module for display and storage.

2. The large field-of-view adaptive optics retinal imaging system with common optical path beam scanning according to claim 1, characterized in that, the light source module, the adaptive optics module, the beam scanning module, the sight beacon module, the defocus compensation module and the pupil monitoring module are sequentially arranged along an incident optical path;

the light source module is configured to comprise a light source, a collimator and a first beam splitter that are sequentially arranged along the incident optical path, and is configured to output a parallel light beam to the adaptive optics module, wherein the light emitted by the light source passes through the collimator, and is then partially transmitted through the first beam splitter to enter the adaptive optics module;

the adaptive optics module is configured to comprise a second beam splitter, a wavefront corrector, a transmissive or reflective telescope and a wavefront sensor that are sequentially arranged along the incident optical path, and is configured to connect to the beam scanning module, detect and correct wavefront aberration; the parallel light beam output by the light source module, after partially being transmitted through the second beam splitter, is reflected to the transmissive or reflective telescope by the wavefront corrector to enter the beam scanning module; the returning imaging light carrying the aberration information of the human eye and the light intensity information exits from the beam scanning module and enters the transmissive or reflective telescope, and then is reflected to the second beam splitter by the wavefront corrector; part of the imaging light is reflected to the wavefront sensor by the second beam splitter to realize measurement of wavefront aberration, and the rest of the imaging light is transmitted through the second beam splitter to continue to propagate;

the wavefront sensor is configured to receive an imaging light beam containing the aberration information of the human eye and transmit the aberration information to the control module, and the control module is configured to perform wavefront calculation, obtain a wavefront control voltage and output the wavefront control voltage to the wavefront corrector, so as to detect and correct wavefront aberration.

3. The large field-of-view adaptive optics retinal imaging system with common optical path beam scanning according to claim 2, characterized in that, the detection module is configured to comprise a collection lens, a confocal pinhole and a high sensitivity detector, wherein the part of the returning imaging light that is transmitted through the second beam splitter of the adaptive optics module reaches the first beam splitter, and is partially reflected by the first beam splitter to the collection lens, focused by the collection lens and then passes through the confocal pinhole to reach the high sensitivity detector, a photoelectric conversion is performed by the high sensitivity detector to obtain an electrical signal, then the electrical signal is output to the control module for processing to obtain a retinal imaging image, and finally the retinal imaging image is output to the output module for display and storage;

the confocal pinhole is disposed at a focal point of the collection lens.

4. The large field-of-view adaptive optics retinal imaging system with common optical path beam scanning according to claim 3, characterized in that the first scanning mirror and the second scanning mirror can have their front and rear positions interchanged;

the beam scanning module is controlled by a voltage signal output from the control module and is configurable in different scanning modes for carrying out different imaging functions including a large field-of-view imaging function, a small field-of-view high-resolution imaging function and a large field-of-view high-resolution imaging function.

5. The large field-of-view adaptive optics retinal imaging system with common optical path beam scanning according to claim 2, characterized in that, the defocus compensation module is configured to comprise a scanning objective lens, a flat-field objective lens and a guide rail that are sequentially arranged along the incident optical path, the light beam exiting from the beam scanning module propagates to the pupil monitoring module through the defocus compensation module, and the flat-field objective lens can reciprocate along the central axis of the flat-field objective lens on the guide rail to achieve the compensation of refractive error of the human eye.

6. The large field-of-view adaptive optics retinal imaging system with common optical path beam scanning according to claim 2, characterized in that, the sight beacon module is configured to comprise an LED array, a lens and a first dichroic beam splitter, wherein the light emitted by any one of LED beads in the LED array after being lit by the control module propagates through the lens, is reflected by the first dichroic mirror to enter the defocus compensation module, and finally reaches the human eye, so as to allow the human eye to gaze at the luminous LED bead to achieve sight fixation; the light beam exiting from the beam scanning module is transmitted through the first dichroic beam splitter of the sight beacon module, and then enters the defocus compensation module to continue to propagate;

the pupil monitoring module is configured to comprise a ring-shaped LED array, a second dichroic beam splitter, an imaging lens and an area-array detector, wherein the light emitted by the ring-shaped LED array illuminates the pupil of the human eye, and is reflected by the pupil of the human eye, passes through a hollow part of the ring-shaped LED array, is reflected by the second dichroic beam splitter, and is focused by the imaging lens to the area-array detector, the area-array detector is configured to convert light signal into an electrical signal and then output the electrical signal to the control module; the control module is configured to obtain a pupil imaging image and finally output the pupil imaging image to the output module for display and storage.

7. The large field-of-view adaptive optics retinal imaging system with common optical path beam scanning according to claim 2, characterized in that, the wavefront sensor included in the adaptive optics module is one of a micro-prism array Hartmann wavefront sensor, a microlens array Hartmann wavefront sensor, a quadrangular pyramid sensor and a curvature sensor, and the wavefront corrector is one of a deformable reflection mirror, a liquid crystal spatial light modulator, a micromachined membrane deformable mirror, a micro-electromechanical deformable mirror, a dual piezoelectric ceramic deformable mirror and a liquid deformable mirror;

95% of the parallel light beam output by the light source module is transmitted through the second beam splitter to the wavefront corrector; the returning imaging light beam is reflected by the wavefront corrector to the second beam splitter, wherein 5% of the light energy of the returning imaging light beam is reflected by the second beam splitter into the wavefront sensor for measuring wavefront aberration, and the remaining 95% of the light energy of the returning imaging light beam is transmitted through the second beam splitter to the first beam splitter to continue to propagate.

8. The large field-of-view adaptive optics retinal imaging system with common optical path beam scanning according to claim 1, characterized in that, the light source module includes a plurality of light sources, wherein the lights emitted from the plurality of light sources are coupled by an optical-fiber coupler and go into a collimator to be collimated into a parallel light beam, or wherein the lights emitted from the plurality of light sources are collimated by corresponding collimators respectively into parallel light beams which are then coupled by a dichroic beam splitter to enter the optical path;

the collimator is a single lens, an achromatic lens, an apochromatic lens or a parabolic reflector for collimating the light beam emitted by the light source into a parallel light beam;

the first beam splitter is a broadband beam splitter, wherein 20% of the parallel light beam exiting from the collimator is transmitted through the beam splitter and continues to propagate into the adaptive optics module, and 80% of the returning imaging light beam exiting from the adaptive optics module is reflected by the first beam splitter to enter the detection module.

9. A large field-of-view adaptive optics retinal imaging method with common optical path beam scanning, characterized in that, the method employs the system according to claim 1 for imaging, and comprises the following steps:

Step S1: turning on and starting the system;
Step S2: placing the subject's head on a headrest bracket, turning on the pupil monitoring module, and manually adjusting the headrest bracket or using the control module to automatically adjust the headrest bracket to translate in three-dimensional way, so that the pupil is imaged in a central area of the field of view;
Step S3: manually sliding the flat-field objective lens along the central optical axis thereof, or using the control module to drive a motor to move the position of the flat-field objective lens on the guide rail, so as to compensate and correct refractive error of the human eye;
Step S4: lighting one LED bead of an LED array in the sight beacon module, so as to allow the subject to gaze at the light spot to achieve sight fixation;
Step S5: switching the adaptive optics module into a shutdown state or a non-working power-on state, setting the beam scanning module to the large field-of-view scanning mode, and using the control module to control the beam scanning module to perform large field-of-view scanning to obtain a large field-of-view imaging image of the retina which is output to the output module;
Step S6: switching the adaptive optics module into a power-on working state to measure and correct wavefront aberration, and using the control module to control the beam scanning module to perform small field-of-view scanning which includes two small field-of-view scanning modes S61 and S62;
Step S61: using the control module to control the beam scanning module to obtain a small field-of-view high-resolution imaging image which is output to the output module;
Step S62: using the control module to control the beam scanning module to obtain a large field-of-view high-resolution imaging image which is output to the output module;
wherein the sequence of Step S5 and Step S6 can be reversed, and Step S61 and Step S62 are selectable to be performed without a particular sequential relation.

* * * * *

UNITED STATES PATENT AND TRADEMARK OFFICE
CERTIFICATE OF CORRECTION

PATENT NO. : 12,004,813 B2
APPLICATION NO. : 16/977192
DATED : June 11, 2024
INVENTOR(S) : Guohua Shi et al.

Page 1 of 1

It is certified that error appears in the above-identified patent and that said Letters Patent is hereby corrected as shown below:

In the Claims

<u>At Column 20</u>
In Claim 1, Line 3, please delete "morror" and replace with -- mirror --.
In Claim 1, Line 10, please delete "retinal" and replace with -- retina --.
In Claim 1, Line 27, please delete "positioin" and replace with -- position --.

Signed and Sealed this
Twenty-seventh Day of August, 2024

Katherine Kelly Vidal
*Director of the United States Patent and Trademark Office*